United States Patent [19]

Freeman et al.

[11] Patent Number: 4,738,256
[45] Date of Patent: Apr. 19, 1988

[54] SURGICAL TOOL

[75] Inventors: Michael A. R. Freeman, London; Michael A. Tuke, Guildford, both of England

[73] Assignee: Finsbury (Instruments) Limited, London, England

[21] Appl. No.: 879,204

[22] Filed: Jun. 26, 1986

[30] Foreign Application Priority Data

Jun. 26, 1985 [GB] United Kingdom ................ 8516167

[51] Int. Cl.⁴ ............................................. A61F 5/04
[52] U.S. Cl. ............................. 128/92 VV; 128/92 R; 128/305
[58] Field of Search ........... 128/92 VD, 92 VJ, 92 V, 128/92 VV, 92 VY, 92 VW, 305, 303 R, 92 R

[56] References Cited

U.S. PATENT DOCUMENTS

| 2,785,673 | 3/1957 | Anderson | 128/92 VJ |
| 3,815,590 | 6/1974 | Deyerle | 128/92 VD |
| 4,103,683 | 8/1978 | Neufeld | 128/92 VD |
| 4,187,559 | 2/1980 | Grell et al. | 128/92 VJ |
| 4,587,964 | 5/1986 | Walker et al. | 128/92 VJ |
| 4,622,959 | 11/1986 | Marcus | 128/92 VD |

Primary Examiner—C. Fred Rosenbaum
Assistant Examiner—Colleen Reilly
Attorney, Agent, or Firm—Lee, Smith & Zickert

[57] ABSTRACT

A surgical tool, for use in hip replacement operations comprises a substantially linear stem which in use seats within a preformed femur cavity. A fixed arm extends medially from an upper portion of the stem and terminates in support for a rotatable cutter. One end of the cutter is received in a seating on the stem below the fixed arm. Ancilliary equipment includes a depth locating tool, so correctly positioning the hip implant in relation to the retained femur neck.

10 Claims, 5 Drawing Sheets

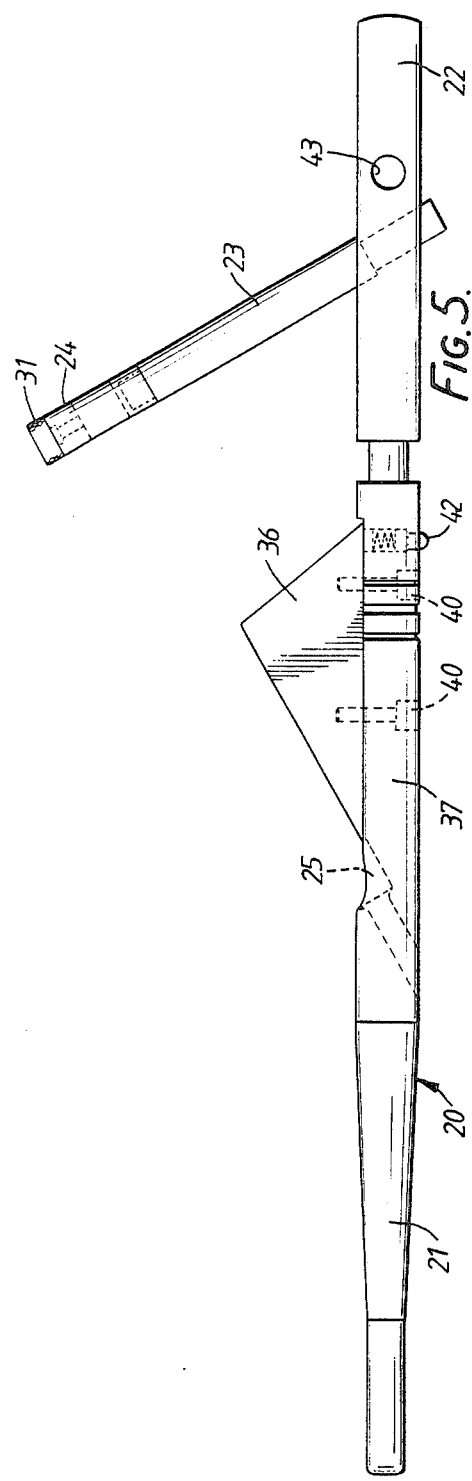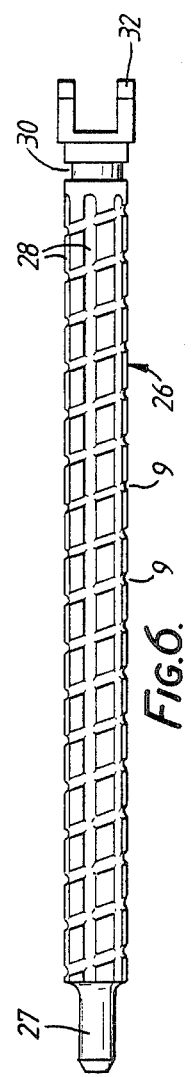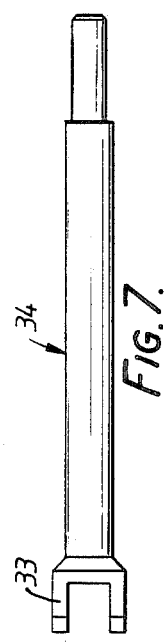

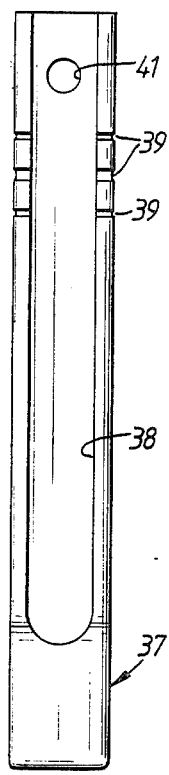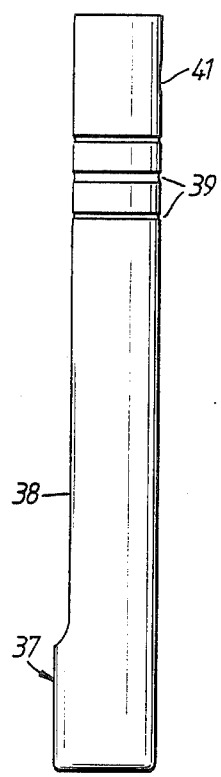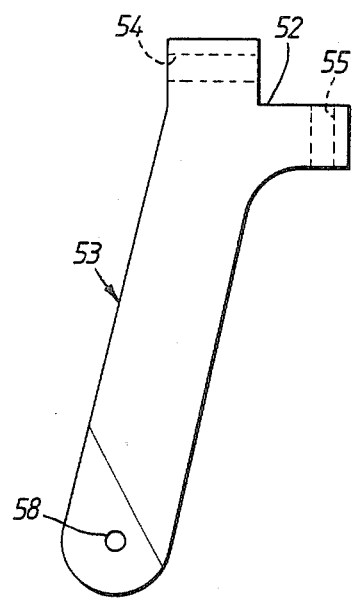
FIG.8.  FIG.9.  FIG.12.
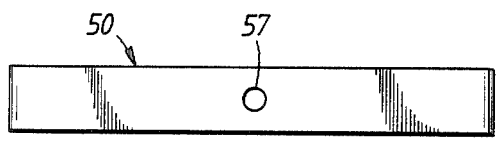
FIG.10.
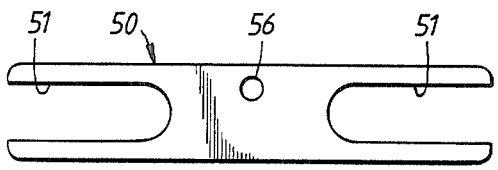
FIG.11.

SURGICAL TOOL

FIELD OF THE INVENTION

This invention relates to surgical tools intended for use in hip replacement operations in which a portion of the femur including the ball head is replaced by an artifical implant.

BACKGROUND OF THE INVENTION

The efficient functioning of the hip joints is extremely important to the well being and mobility of the human body. Each hip joint is constituted by the upper portion of the upper leg bone (femur) which terminates in an offset bony neck surmounted by a ball-headed portion which rotates within a socket (acetabulum) in the hip bone. Diseases such as rheumatoid- and osteo-arthritis can cause erosion of the cartilage lining the acetabulum so that the ball of the femur and hip bone rub together causing pain and further erosion. Bone erosion causes the bones themselves to attempt to compensate and reshape, thus giving a misshapen joint which may well cease to function altogether.

The replacement of the hip joint by an artificial implant is widely practised, but the implants conventionally used and the conventional methods of implantation can suffer from a number of disadvantages.

Thus, conventional hip implants are usually inserted by resecting the neck of the femur and reaming a comparatively large cavity down the femur to receive a bow-shaped implant surmounted by a ball which is then cemented in place using, for example, an acrylic filler material. The implant is bow-shaped to correspond to the angle which the intact femur ball head makes with the downwardly extending stem of the femur. Examples of such hip implants are shown in GB Patent Specification Nos. 1409053 and 1409054.

It will be appreciated that such an operation requires great skill and expertise on the part of the surgeon who must, for example, use one or more bow shaped rasps of increasing size in an effort to locate the canal down the femur and to create a cavity which, at best, can only approximate to the shape of the implant and which requires cement to secure the implant within the cavity. Furthermore, this can lead to errors in positioning the ball head with respect to the acetabulum or femur, thus preventing the normal range of hip movement and/or causing unwanted bone impaction or uneven leg length.

The bottom portion of the implant, while tapering, is conventionally of non-circular flattened cross-section so as to resist rotational forces within the reamed cavity. Such an implant, if correctly cemented can be comparatively efficient but, if not correctly cemented, or after a long period of use, the cement may work loose, thus allowing movement of the implant and causing bone erosion. Bone erosion can lead to tissue reactions which themselves can lead to further bone destruction. As a result, the joint can be damaged beyond repair.

GB patent Specification No. 1489887 discloses an implant which has a substantially linear stem which is grooved to assist in anchoring the stem in the femur and which stem flares medially at its upper end to give a comparatively thick upper portion terminating in a shoulder and ball head. In use, the neck of the femur is resected and the shoulder rests on the cut edge of the femur. There is thus very little bone retention in the upper part of the femur. The specification discloses the use of drills and a milling cutter for forming the desired femur cavity. The milling cutter makes a medial cut in what little remains of the femur neck by being progressively moved down a guide rod in a pre-drilled bore down the femur stem. The junction between the medial cut and the pre-drilled bore cannot be accurately machined in this manner and the device is only suitable for producing a cut of considerable width and shallow depth, which is all that is necessary when most or all of the bony neck of the femur has been removed.

The practice of removing almost completely the bony neck of the femur, as illustrated in GB No. 1489887, is destructive of bone and against the accepted advantages of conserving as much bone as possible.

A further result of the shape of conventional implants and the removal of much of the bony neck (which in a healthy hip bone provides reinforcement) is the problem of so-called "stress shielding". Thus, with a conventional implant, both compression and torsional loads are being borne by the lower portion of the implant projecting down the stem of the femur and not by the upper bowed portion adjacent the ball. This can lead to fatigue failure of the implant itself and/or undue loading of the adjacent portions of the femur. Because the remaining uppermost portions of the femur are shielded from load they themselves may start to disappear.

These problems with existing implants have led to the development of implants which can be employed without using cement. Such an implant is described in European Patent Application Publication No. 0158534 and comprises a stem portion with a substantially linear axis, at least the lower portion of the stem having a substantially circular cross-section. A wedge shaped portion extends medially from the stem at or near the upper end and is surmounted by a ball head. The wedge shaped portion, preferably of flattened section, thus lodges in use within the bony neck of the femur, most of which can therefore be retained. This ensures maximum bone conservation and assists in overcoming the problems of stress shielding. The linear nature of the stem and the circular cross section ensure that the implant can be readily withdrawn for replacement simply by cutting any bone grafting which has occurred towards the top of the implant in the region of the wedge portion. It is possible to employ such an implant without the use of cement, but this naturally assumes that the cavity for the implant can be accurately prepared, both down the main stem of the femur and in the region of the bony neck.

OBJECTS OF THE INVENTION

It is an object of the invention to provide a surgical tool suitable for use during preparation of an accurate cavity to receive a hip implant of the type described above.

It is a further object of the invention to provide a combination of such a surgical tool with a depth locating tool and, optionally with further tools, for the preparation of an acurate cavity to receive a hip implant of the type described above.

It is still a further object of the invention to provide a surgical tool or a combination of tools for the preparation of an accurate cavity to receive a hip implant with minimal bone destruction.

SUMMARY OF THE INVENTION

According to this invention we provide a surgical tool, intended for use in hip replacement operations, having a substantially linear locating stem which is adapted in use to seat within a preformed cavity in a femur, and a fixed arm extending medially from an upper portion of the stem terminating in support means for a rotatable cutter, the stem having a seating below the arm capable of receiving one end of the rotatable cutter, the conformation of the stem and the cutter, when mounted in the support means and seating, generally corresponding to the conformation of the upper portion, including the neck, of a femur.

According to a further aspect of the invention we provide a surgical tool as described above in combination with a depth locating tool comprising a fork portion which, in use, can adjustably engage an upper portion of the stem and an offset and medially extending side plate carried by the fork portion and provided with a marker device projecting rearwardly of the plate in a direction generally parallel to the plane of the fork portion and, in use, intended to lodge below the neck of the femur.

BRIEF DESCRIPTION OF THE DRAWINGS

FIG. 5 is a plan view of the surgical tool of the invention without its associated cutter;

FIG. 6 is a plan view of a cutter;

FIG. 7 is a plan view of the operating shaft of the cutter of FIG. 6;

FIGS. 8 and 9 are views at right angles to each other of a sleeve for the surgical tool of FIG. 5;

FIGS. 10 and 11 are respectively a top view and side view of a first part of a depth locating tool for use with the surgical tool of FIG. 5; and FIG. 12 is a side view of a second part of the depth locating tool of FIGS. 10 and 11;

DESCRIPTION OF THE PREFERRED EMBODIMENTS

Preferably a wedge shaped guide portion is provided on the stem in the angle between the stem and the cutter adjacent the seating to ensure that cutting occurs within a single plane.

The cutter may have any suitable cutting conformation such as longitudinal and/or helical cutting edges, and may have a varying diameter, e.g. it may be trumpet shaped. It may be hand operated by provision of suitable operating means attached for example by a universal joint to its upper end. The cutter may be adapted to be employed within the seating at all times, or, alternatively, a separate cutting tool which is advanced through the support means towards the seating may be employed.

Preferably one or more sleeves are provided to lodge over the stem to vary its diameter dependent on the size of implant to be used.

The surgical tool of the invention is preferably used in conjuction with a depth locating tool comprising a fork portion, which, in use, can adjustably engage an upper portion of the stem and an offset and medially extending side plate carried by the fork portion and provided with a marker device projecting rearwardly of the plate in a direction generally parallel to the plane of the fork portion and, in use, intended to lodge below the neck of the femur. Suitably the marker device is a pin projecting rearwardly of a downwardly directed portion of the side plate. A finding rod may be provided adapted to locate and enter the femur canal. The marker pin can be positioned by sliding the depth locating tool on the finding rod until the pin lodges below the lower face of the femur neck. The position of the device on the rod thus indicates the maximum depth of cavity allowable to receive an implant which extends into the neck of the femur without projecting therefrom. At least one reaming device may also be provided for reaming a substantially linear cavity in the femur stem. The reaming device may also slidably carry the depth locating tool.

One form of the invention will now be described by way of example with reference to the accompanying drawings.

The surgical tool of the invention is intended to assist in forming an accurate cavity for insertion of an implant as shown in FIGS. 1 to 5.

Figures 1, 2, 3:
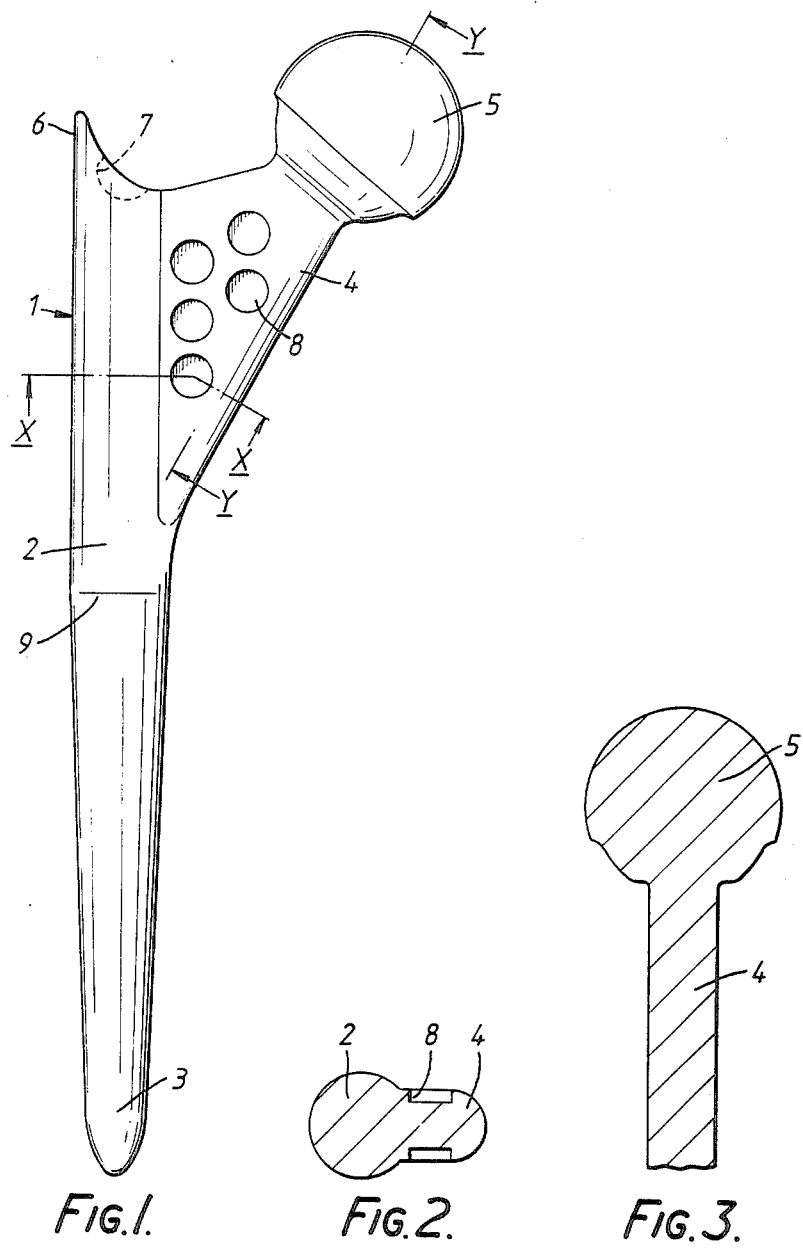
FIG. 1 is a side view of an implant to be inserted with the aid of a tool according to the invention.
FIG. 2 is a section on line X—X of FIG. 1.
FIG. 3 is a partial section on line Y—Y of FIG. 1.

The implant 1, of suitable material acceptable to the human body such as a cobalt-chromium alloy or titanium alloy, comprises a stem 2 which has a substantially linear axis and a substantially circular cross-section as can be seen from FIG. 2. The stem 2 tapers towards its lower end 3, the extent of the taper or even absence of any taper depending on individual needs. Spaced from the tapered portion 3, a flattened wedge portion 4 extends medially (i.e. in use, towards the middle of the body) from the stem 2 and is surmounted by a ball head 5 which may be separable to adjust neck length for individual needs. The stem 2 extends beyond the wedge portion 4 to form a projecting end 6 for lateral support and provided with an aperture 7, which, in use, can receive a hook or like means for removing the implant from the bone if this becomes necessary. Wedge portion 4 is provided with indentations 8 which, when the implant is in place, can assist in encouraging bone interlock, e.g. by grafting of the adjacent bone to the implant 1. Wedge portion 4 may also be gradually reduced in thickness from the proximal to the distal end to assist interference interlock with the bone, especially when the wedge portion has a textured surface.

Figure 4:
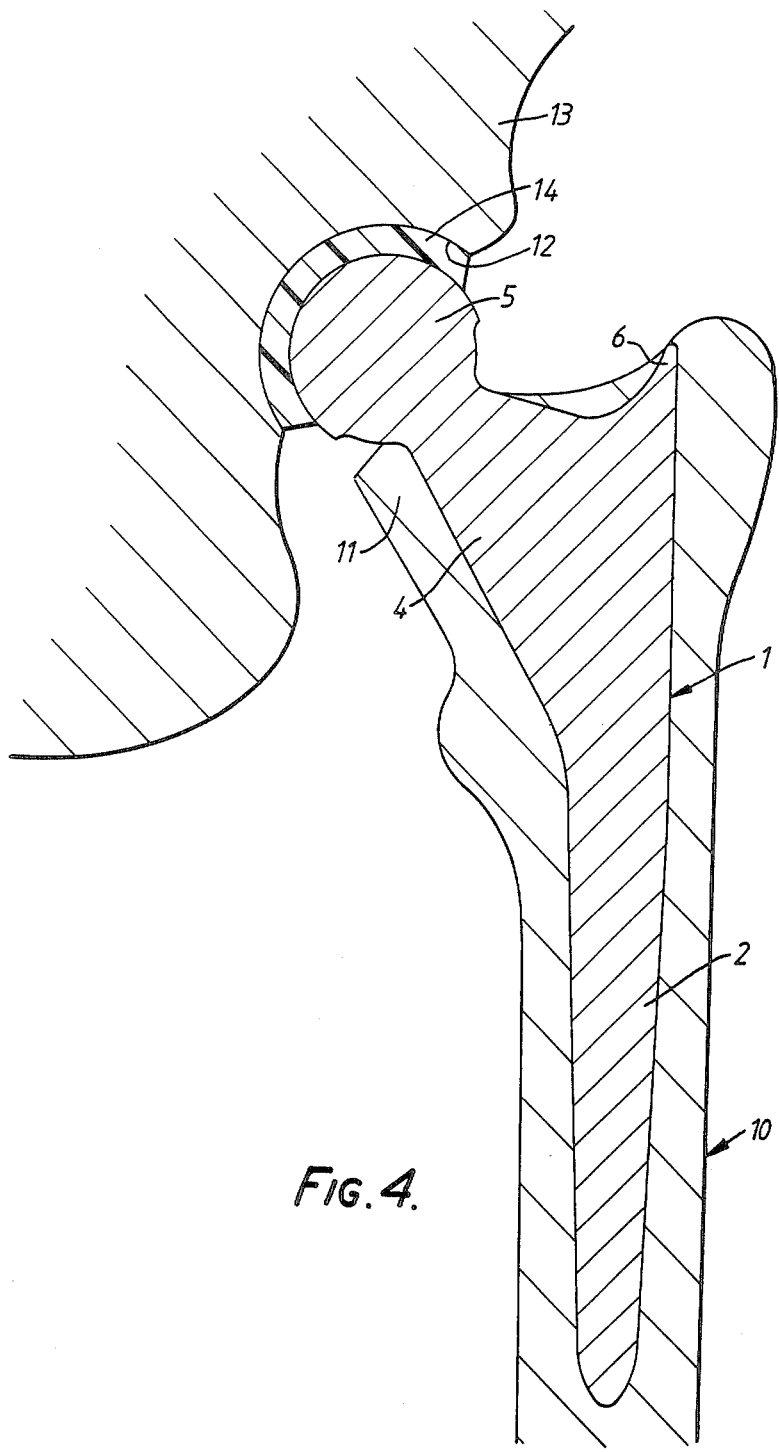
FIG. 4 is a side view of a hip joint incorporating the implant of FIG. 1.

FIG. 4 illustrates the position occupied by the implant when in use in a human body. Thus the femur 10 of a human body has had the ball removed from the top of the bony neck 11. It is to be particularly noted that most of the bony neck remains intact throughout its length except for a slot entering its superior surface and that the distal part of the femoral head is also retained. The ball head 5 of the implant 1 projects from the neck 11 within the acetabulum 12 formed in the hip bone 13. The acetabulum may contain a synthetic lining insert 14 of suitable physiologically acceptable synthetic material to replace the worn cartilage of the joint and provide a bearing surface for the ball head 5.

The implant has been introduced by first accurately reaming an aperture down the femur 10 as described below and then providing an accurately machined slot in the neck 11 of the femur with bone only removed to the extent necessary to receive the comparatively thin wedge portion 4 of the implant.

This latter slot formation can be accomplished using the surgical tool shown in FIGS. 5 to 9 and 15 which comprises a linear locating stem 20 which tapers towards one end 21 (which will be lowermost in use)

and which has towards its upper end 22 a fixed projecting arm 23 which projects from the stem 20 in a medial direction in use and has at its extremity a supporting ring 24. Stem 20 is also provided towards its tapered end 21 with a recess 25, which in use provides a seating for one narrowed end 27 of a cutter 26, best seen in FIG. 6. Cutter 26 is provided with longitudinally extending flutes 28 and a helical groove 29 but any suitable cutting conformation giving adequate clearance of debris during use is suitable. Cutter 26 is adapted to extend from recess 25 so that a neck 30 at the opposite end to narrowed end 27, passes through ring 24, the neck 30 being engageable by a knurl headed screw 31 passing through a bore in ring 24 so that the cutter 26 is held against longitudinal displacement but can rotate within recess 25 and ring 24. Cutter 26 has a fork head 32 to receive a corresponding head 33 of an operating shaft 34 shown in FIG. 8. Shaft 34 can be adjusted to any suitable angle to allow convenient rotation of the cutter 26.

Stem 20 has projecting medially therefrom a comparatively thin wedge-shaped block 36 held to stem 20 by screws 40. In addition a series of sleeves such as that shown at 37 in FIGS. 5, 8, 9 and 15 are provided, which can engage over the middle portion of stem 20 to increase the diameter to accommodate to different cavity sizes. The sleeve 37 has a longitudinally extending slot 38 to allow passage of wedge block 36 and a series of grooves 39 whose purpose is to give a secondary indication of the depth of penetration of the stem in use. The base of sleeve 37 at the end which will be uppermost in use has a hole 41 with which engages a spring loaded ball catch 42 so that the sleeve 37 is held securely on stem 20. Stem 20 is also provided at its upper end with an aperture 43 which, in use, can receive a tommy bar (not shown) to assist the surgeon in holding the tool.

FIGS. 10 to 15 illustrate a depth locating tool intended for use prior to and during use of the tool shown in FIGS. 5 to 9 to determine the depth to which the cut is to be made. The depth locating tool comprises a fork portion 50 having two opposite forked ends 51 which can slidably engage the upper portion of a finding rod (FIG. 13), a reaming device (FIG. 14) or the stem 20 of the tool described above (FIG. 15). Fork portion 50 is intended in use to lodge transversely within angle 52 in a side plate 53 which thus extends medially from the portion 50 and in a plane at right angles to the plane of portion 50. Portion 50 and plate 53 are suitably attached by screws or the like at positions 54 and 55 on plate 53 which mate with positions 56 and 57 respectively of the fork portion 50. The lower offset end of plate 53 carries a locating pin 58 extending parallel to fork portion 50 but offset from and below fork portion 50. The purpose of the tool of FIGS. 10, 11 and 12 is described below.

Figure 13:
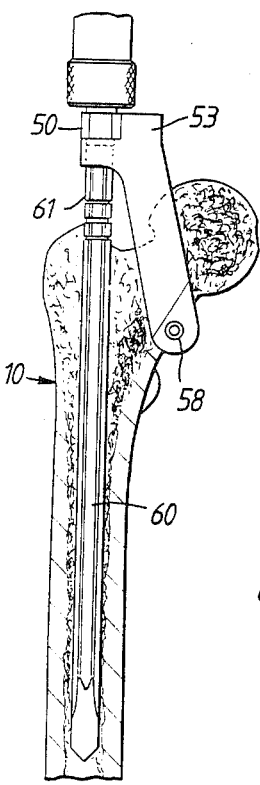
FIGS. 13, 14 and 15 are side views illustrating progressive stages in a hip implantation operation.

The use of the tool of FIGS. 5 to 9 in conjunction with the tool of FIGS. 10, 11 and 12, will now be described with reference to FIGS. 13, 14 and 15. In carrying out a hip implant operation with the intention of inserting an implant as shown in FIGS. 1 to 4, the first step is to use a finding rod 60 (FIG. 13) to locate the position of the central canal down the length of the femur 10. The locating tool of FIGS. 10, 11 and 12 is employed to determine the depth to which a cavity is to be prepared by placing one of the forked ends (dependent on whether the operation is on a right or left hip) over the projecting upper portion 61 of the finding rod 60 and adjusting the device until pin 58 comes to rest just below the lower face of the neck 11 of the femur.

The position is noted on a scale on the finding rod 60 and thus gives the maximum allowable depth to which the implant 1 can be inserted while still safely retaining its wedge portion 4 within bony neck 11.

Figure 14:
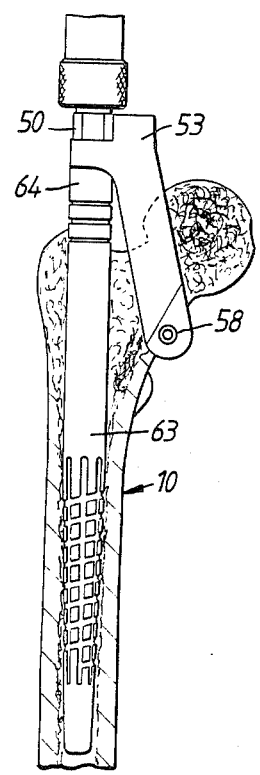

Next, as illustrated in FIG. 14, a substantially linear cavity is reamed down the femur 10 to the predetermined depth, using a reamer such as that shown at 63, increasing the size of the reamer used as necessary until a cavity is produced with a suitable taper dependent on the bone itself and the size of the canal, the object being to ensure that the lower end of the implant is in contact with strong bone. Again the depth locating tool is positioned on the projecting end 64 of reamer 63 to ensure that the cavity is of the required depth so that the inserted implant will have its wedge portion within the neck 11. Thus the diameter of implant stem 2 has now been determined.

Figure 15:
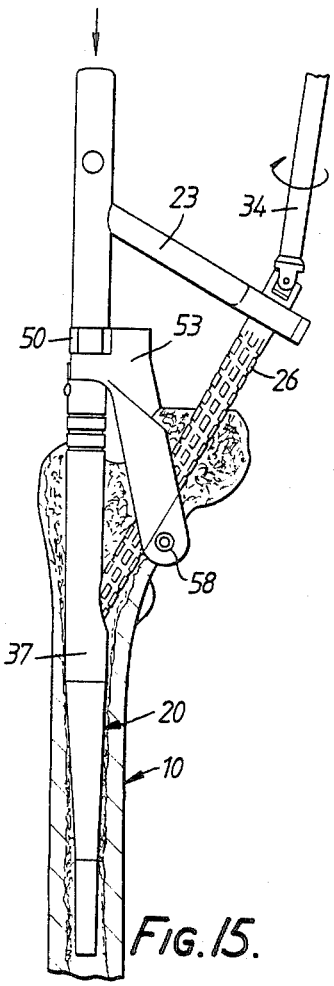

The tool of FIGS. 5 to 9 is then employed as shown in FIG. 15, after attachment of the correct sheath 37 to correspond to the determined implant diameter so that locating stem 20 of the tool slides securely into the preformed cavity as the tool is advanced with cutter 26 being rotated to machine the necessary slot in neck 11 to eventually receive wedge portion 4 of the implant. Again the depth locating tool is employed with fork 50 engaged on the projecting portion of stem 20 to ensure that the cutter is advanced to the correct depth and no further.

While it is most suitable to initially position the lower portion of stem 20 in the top portion of the pre-reamed cavity and then advance the tool with the cutter rotatably held in seating 25 and ring 24, it will be appreciated that the complete stem 20 could be inserted in the cavity and the cutter advanced from the ring 24 towards the seating 25. However in this case one would need to dispense with wedge 36 which normally acts as a valuable guide to keep the machined slot in a single plane and subsequent sawing would be necessary to complete the slot.

Finally, the remaining femur ball held and as little bony neck as possible is resected and the implant fitted.

We claim:

1. A surgical tool, intended for use in a hip replacement operation in a patient in the course of which at least a part of the front side and at least a part of the medial side of the patient's femur are exposed to permit hip replacement to be performed, the surgical tool comprising:
    a substantially linear locating stem, intended in use to seat within a preformed cavity in a femur of a patient requiring a hip replacement operation;
    a rotatable cutter; and
    means for mounting the rotatable cutter on the stem;
    the mounting means comprising:
        a fixed arm extending laterally from an upper portion of the stem in a direction which, in use, is medial to the patient's femur;
        support means for the rotatable cutter terminating the fixed arm; and
        a seating on the stem below the arm capable of receiving one end of the rotatable cutter;
        the arrangement being such that the conformation of the stem and cutter, when mounted in the support means and seating, generally corresponds to the conformation of the upper portion, including the neck, of a femur.

2. The surgical tool of to claim 1, further comprising:

a wedge shaped portion, provided on the stem in the angle between the stem and the cutter and adjacent the seating.

3. The surgical tool of claim 1, wherein the support means is arranged so that one end of the cutter is permanently mounted within the seating.

4. The surgical tool of claim 1, wherein the rotatable cutter has longitudinal and/or helical cutting edges.

5. The surgical tool of claim 1, wherein the rotatable cutter has means at that end distal from the seating to receive operating means for the cutter.

6. The surgical tool according to claim 1 further comprising:
   at least one sleeve adapted to lodge over the stem to vary the effective diameter of the stem.

7. A surgical tool in combination with a depth locating tool, the combination being intended for use in a hip replacement operation in a patient in the course of which at least a part of the front side and at least a part of the medial side of the patient's femur are exposed to permit hip replacement to be performed, the surgical tool comprising:
   a substantially linear locating stem, intended in use to seat within a preformed cavity in a femur of a patient requiring a hip replacement operation;
   a rotatable cutter; and
   means for mounting the rotatable cutter on the stem;
   the mounting means comprising:
      a fixed arm extending laterally from an upper portion of the stem in a direction which, in use, is medial to the patient's femur;
      support means for the rotatable cutter terminating the fixed arm; and
      a seating on the stem below the arm capable of receiving one end of the rotatable cutter;
      the arrangement being such that the conformation of the stem and the cutter, when mounted in the support means and seating, generally corresponds to the conformation of the upper portion, including the neck, of a femur; and the depth locating tool comprising:
   a fork portion which in use adjustably engages the upper portion of the stem of the surgical tool;
   an offset side plate which is carried by and extends laterally from the fork portion in a direction which, in use, is medial to the patient's femur; and
   a marker device which is mounted on the plate, which, in use, projects rearwardly of the patient's femur from the plate in a direction generally parallel to the plane of the fork portion and which is, in use, intended to lodge below the neck of the femur.

8. The combination of claim 7 wherein the side plate has a downwardly directed portion and the marker device is a pin projecting rearwardly of the downwardly directed portion.

9. The combination of claim 7 in further combination with a finding rod adapted to enter the canal of the femur and capable of slidably carrying the depth locating tool.

10. An assembly of tools for use in a hip replacement operation in a patient in the course of which at least a part of the front side and at least a part of the medial side of the patient's femur are exposed to permit hip replacement to be performed, the assembly comprising:
(A) a surgical tool comprising:
   a substantially linear locating stem, intended in use to seat within a preformed cavity in a femur of a patient requiring a hip replacement operation;
   a rotatable cutter; and
   means for mounting the rotatable cutter on the stem;
      the mounting means comprising:
         a fixed arm extending laterally from an upper portion of the stem in a direction which, in use, is medial to the patient's femur;
         support means for the rotatable cutter terminating the fixed arm; and
         a seating on the stem below the arm capable of receiving one end of the rotatable cutter;
         the arrangement being such that the conformation of the stem and the cutter, when mounted in the support means and seating, generally corresponds to the conformation of the upper portion, including the neck, of a femur;
(B) a depth locating tool comprising:
   a fork portion which in use adjustably engages the upper portion of the stem of the surgical tool;
   an offset side plate which is carried by and extends laterally from the fork portion in a direction which, in use, is medial to the patient's femur; and
   a marker device which is mounted on the plate, which, in use, projects rearwardly of the patient's femur from the plate in a direction generally parallel to the plane of the fork portion and which is, in use intended to lodge below the neck of the femur;
(C) a finding rod adapted to enter the canal of a femur and capable of slidably carrying the depth locating tool; and
(D) at least one substantially linear reaming device, adapted to ream a desired substantially linear cavity in the femur stem and capable of slidably carrying the depth locating tool.

* * * * *